United States Patent [19]

Gigliotti et al.

[11] Patent Number: 4,467,108
[45] Date of Patent: Aug. 21, 1984

[54] PROCESS FOR THE PREPARATION OF 3-METHYL-3-HYDROXY-GLUTARIC ACID

[75] Inventors: Guiseppe Gigliotti, Paris; Jean-Michel Roul, Chelles, both of France

[73] Assignee: Roussel Uclaf, Paris, France

[21] Appl. No.: 498,834

[22] Filed: May 27, 1983

[30] Foreign Application Priority Data

Jun. 17, 1982 [FR] France .................. 82 10597

[51] Int. Cl.³ ............................................. C07C 69/66
[52] U.S. Cl. ..................................... 560/180; 562/582
[58] Field of Search ..................... 560/180; 562/582

[56] References Cited

U.S. PATENT DOCUMENTS

| | | | |
|---|---|---|---|
| 2,496,791 | 2/1950 | Hagemeyer | 560/180 |
| 2,904,555 | 9/1959 | Kodras | 562/582 |
| 3,647,890 | 3/1972 | Kreevoy | 560/180 |
| 4,208,204 | 6/1980 | Yavrouian | 560/180 |

*Primary Examiner*—Paul J. Killos
*Attorney, Agent, or Firm*—Charles A. Muserlian

[57] ABSTRACT

A novel process for the preparation of 3-methyl-3-hydroxy-glutaric acid of the formula

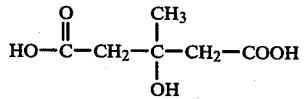

I comprising reacting a compound of the formula

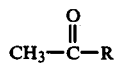

II wherein R is selected from the group consisting of alkoxy of 1 to 6 carbon atoms, formyloxy, halogen and acyloxy of 2 to 18 carbon atoms with at least two equivalents of a compound of the formula

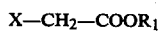

III wherein X is an alkali metal and $R_1$ is alkyl of 1 to 6 carbon atoms to obtain a compound of the formula

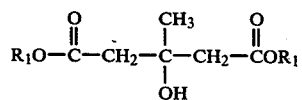

IV and subjecting the latter to saponification or optionally catalytic thermal decomposition to obtain 3-methyl-3-hydroxy-glutaric acid and a novel intermediate.

8 Claims, No Drawings

PROCESS FOR THE PREPARATION OF 3-METHYL-3-HYDROXY-GLUTARIC ACID

STATE OF THE ART

U.S. Pat. No. 3,818,080 describes 3-hydroxy-glutaric acid and U.S. Pat. No. 3,629,449 describes 3-methyl-3-hydroxy-glutaric acid and its use as a hypocholesterolemiant and hypolipemiant. U.S. Pat. No. 4,105,794 describes the use of 3-methyl-3-hydroxy-glutaric acid in the treatment of biliairy calculs.

French Pat. No. 2,411,822 describes the preparation of 3-methyl-3-hydroxy-glutaric acid by oxidation with an interface catalyst of the compound of the formula

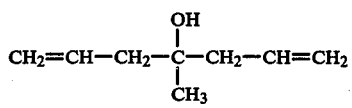
                        A but the yields are unsatisfactory. Bioch. Preparations, Vol. 16 (1958), p. 25 describes an oxidation cleavage of compound A. The use of ozone presents many difficulties for adaptation to a commerical scale and is a particularly dangerous type of reactant. For instance, Milles [Chem. Eng. News, Vol. 51(6), p. 29]reports on the effect of an explosion when using this method.

Another recent method for the preparation of 3-methyl-3-hydroxy glutaric acid described in Synthesis, Vol. 10, (Oct., 1981), p. 791 has the following reaction scheme:

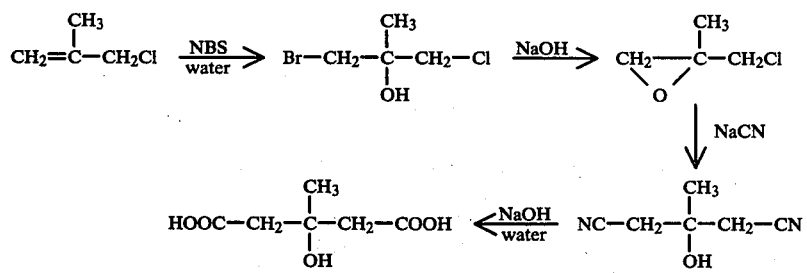

OBJECT OF THE INVENTION

It is an object of the invention to provide an improved process for the preparation of 3-methyl-3-hydroxy-glutaric acid.

It is another object of the invention to provide a novel intermediate product.

These and other objects and advantages of the invention will become obvious from the following detailed description.

THE INVENTION

The novel process of the invention for the preparation of 3-methyl-3-hydroxy-glutaric acid of the formula

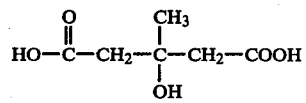
                        I comprises reacting a compound of the formula

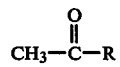
                      II wherein R is selected from the group consisting of alkoxy of 1 to 6 carbon atoms, formyloxy, halogen and acyloxy of 2 to 18 carbon atoms with at least two equivalents of a compound of the formula

X—CH$_2$—COOR$_1$            III wherein X is an alkali metal and R$_1$ is alkyl of 1 to 6 carbon atoms to obtain a compound of the formula

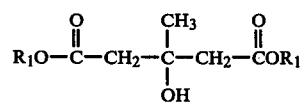
                      IV and subjecting the latter to saponification or optionally catalytic thermal decomposition to obtain 3-methyl-3-hydroxy-glutaric acid.

In the compounds of formula II, examples of R are alkoxy such as methoxy, ethoxy, propoxy, isopropoxy, butoxy, isobutoxy, sec.-butoxy, tert.-butoxy, pentoxy, isopentoxy, sec.-pentoxy, tert.-amyloxy, neopentoxy and hexyloxy; formyloxy, acyloxy such as acetyloxy, propionyloxy, butyryloxy, isobutyryloxy, pivaloyloxy, undecanoyloxy, acryloyloxy, crotonoyloxy, cyclopropylcarbonyloxy, cyclobutylcarbonyloxy, cyclopentylcarbonyloxy, cyclohexylacetyloxy, cyclohexylpropionyloxy, benzoyloxy, phenylacetyloxy and phenylpropionyloxy; and halogens such as chlorine, bromine and iodine.

Examples of X in the compounds of formula III are alkali metals such as sodium, potassium and lithium and examples of R$_1$ are alkyl such as methyl, ethyl, propyl, isopropyl, butyl, isobutyl, tert.-butyl, sec.-butyl, pentyl, isopentyl, sec.-pentyl, tert.-amyl, neopentyl and hexyl.

The saponification of the compounds of formula IV is preferably effected with a base such as sodium hydroxide, potassium hydroxide or barium oxide and the saponification is followed by reacidification with an acid such as sulfuric acid or hydrochloric acid.

The thermal decomposition is effected by heating at a temperature on the order of 150° to 250° C., preferably about 180° C. The thermal decomposition is preferably catalyzed by an acid such as hydrochloric acid by heating preferably at reflux of an aqueous solution.

In a preferred mode of the preparation of 3-hydroxy-3-methyl-glutaric acid comprises reacting a compound of the formula

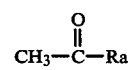
                      IIa wherein Ra is selected from the group consisting of alkoxy of 1 to 4 carbon atoms, halogen and alkanoyloxy of 2 to 4 carbon atoms with at least two molar equivalents of a compound of the formula $$X'-CH_2-COOR_{1a} \qquad \text{IIIa}$$

wherein X' is lithium and $R_{1a}$ is alkyl of 1 to 4 carbon atoms to obtain a compound of the formula

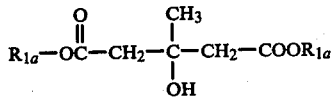

and subjecting the latter to saponification or thermal decomposition with acid catalyst to form 3-methyl-3-hydroxy-glutaric acid.

Particularly preferred in the said process, Ra of the compound of formula IIa is methoxy, ethoxy, acetyloxy or chlorine and X' is lithium and $R_{1a}$ of the compound of formula IIIa is methyl, ethyl or tert.-butyl. The saponification of the compound of formula IVa is preferably effected with aqueous sodium hydroxide solution. Most preferably, Ra is chlorine or acetyloxy and $R_{1a}$ is tert.-butyl and X' is lithium.

The process is still effected preferentially by reacting the compounds of formulae IIa and IIIa at 0° to −80° C. in at least one solvent selected from the group consisting of tetrahydrofuran, dimethylformamide, hexamethylphosphotriamide and methylcyclohexane.

Another preferred mode of the process of the invention comprises preparing a compound of formula III or IIIa by reacting a strong base with an alkyl acetate in a solvent to obtain the compound of formula III or IIIa in solution which is directly reacted with the compound of formula II or IIa.

The strong base is especially preferred to be a dialkyl-lithium amide prepared in situ by reacting butyllithium with a dialkylamine and preferably diisopropylamine and butyllithium are reacted in a cyclohexane solution to prepare lithium diisopropylamide in situ. However, other strong bases such as sodium amide or potassium tert.-butylate may be used.

A preferred mode of the process comprises adding the compound of formula II or IIa to a solution of the compound of formula III or IIIa in at least one organic solvent selected from the group consisting of tetrahydrofuran, dimethylformamide, methylcyclohexane and hexamethylphosphotriamide at the temperatures indicated above, preferably at about −40° C. The introduction of the compound of formula II or IIa is preferably effected slowly, i.e. over a period up to two hours is possible although it may be as little as 30 minutes. The reaction between the said compounds may be on the order of 10 to 15 hours depending upon the reaction conditions, but under the preferred reaction conditions, a reaction time of about 2 hours is generally sufficient.

The novel intermediate of the invention is the ditert.-butyl ester of 3-methyl-3-hydroxy-glutaric acid.

In the following examples there are described several preferred embodiments to illustrate the invention. However, it should be understood that the invention is not intended to be limited to the specific embodiments.

EXAMPLE 1

Ditert.-butyl 3-methyl-3-hydroxy-glutarate 187 g of a solution of 19.5% butyllithium in cyclohexane (36.4 g of butyllithium) were added over 5 minutes at −40° C. under argon to 500 ml of tetrahydrofuran and then 57.5 g of diisopropylamine were added over 5 minutes at −40° C. The mixture was stirred at −40° C. for 30 minutes and 66 g of tert.-butyl acetate were added thereto at −40° C. The mixture was stirred at −40° C. for 30 minutes and then 27.5 g (≃0.55 mole per mole of tert.-butyl acetate) of ethyl acetate were added at −40° C. over 30 minutes. The mixture was stirred at −40° C. for two hours and the temperature allowed to rise to 20° C. under reduced pressure. The mixture was evaporated to dryness under reduced pressure at 20° C. and the residue was taken up in 200 ml of methylene chloride. The solution was cooled to 0° C. and 100 ml of water were added. The decanted aqueous phase was extracted with methylene chloride and the combined organic phases were adjusted to a pH of 1 by addition of 22° BACU/e/ hydrochloric acid. The organic phase was washed with water, dried and evaporated to dryness under reduced pressure to obtain a lightly colored liquid which was rectified at 1 mm Hg to obtain 25 g of ditert.-butyl 3-methyl-3-hydroxy-glutarate with a boiling point of 95°±' C. at1 mm Hg.

| Analysis: $C_{14}H_{26}O_5$ | | |
|---|---|---|
| | % C | % H |
| Calculated: | 61.29 | 9.55 |
| Found: | 61.3 | 9.5 |

EXAMPLE 2

The procedure of Example 1 was repeated except the ethyl acetate was replaced by 0.55 mole of methyl acetate to obtain the same result.

EXAMPLE 3

The process of Example 1 was repeated a number of times with the following different modifications (A) introduction of ethyl acetate and the stirring was effected at −70° C., (B) introduction of ethyl acetate and stirring was effected at −20° C., (C) introduction of ethyl acetate and stirring was effected at 0° C., (D) tetrahydrofuran was replaced by (a) a mixture of tetrahydrofuran and hexamethylphosphotriamide, (b) a mixture of tetrahydrofuran and dimethylformamide, (c) methylcyclohexane and (d) a mixture of tetrahydrofuran and methylcyclohexane and (E) (a) tert.-butyl acetate was added over 90 minutes followed by stirring for one hour and (b) ethyl acetate was added over two hours followed by stirring for 15 hours.

EXAMPLE 4

Using the procedure of Example 1, the process was repeated by replacing ethyl acetate (a) with tert.-butyl acetate and (b) with acetic acid anhydride.

EXAMPLE 5

The procedure of Example 1 was repeated by replacing tert.-butyl acetate with ethyl acetate and replacing the ethyl acetate with (a) acetic anhydride and (b) acetyl chloride.

EXAMPLE 6

The procedure of Example 1 was repeated by replacing tert.-butyl acetate with methyl acetate and replacing ethyl acetate with acetyl chloride.

EXAMPLE 7

Ditert.-butyl 3-methyl-3-hydroxy-glutarate 935 g of a solution of 19.5% butyllithium in hexane (182.3 g of butyllithium) were added over 15 minutes at −40° C. under nitrogen to 2500 ml of tetrahydrofuran and then 287.5 g of diisopropylamine were added thereto over 20 minutes at −40° C. The mixture stood at −40° C. for 15 minutes and then 330 g of tert.-butyl acetate were added thereto at −40° C. over 30 minutes. The mixture stood at −40° C. for 30 minutes and 122.6 g of acetyl chloride were added thereto at −40° C. over 30 minutes. The mixture was stirred for two hours at −40° C. and the temperature was allowed to rise to 20° C. The mixture was evaporated to dryness under reduced pressure below 25° C. and 1000 ml of methylene chloride were added to the residue at 20° C. with stirring. A mixture of 500 ml of iced water were added at less than 20° C. to the mixture which was adjusted to a pH of 1 by addition of 200 ml of 22° BACU/e/ hydrochloric acid. The decanted aqueous phase was washed twice with 150 ml of methylene chloride and the combined organic phases were washed three times with 500 ml of demineralized water, dried and filtered. The filter was rinsed with methylene chloride and the filtrate was evaporated to dryness under reduced pressure to obtain 337.7 g of ditert.-butyl 3-methyl-3-hydroxy-glutarate.

EXAMPLE 8

3-methyl-3-hydroxy-glutaric acid 6.4 g of ditert.-butyl 3-methyl-3-hydroxy-glutarate were heated at 180° C. for 30 minutes and was cooled to 20° C. to obtain 3.45 g of product which was crystallized from ethyl acetate to obtain 3-methyl-3-hydroxy-glutaric acid melting at 180° C.

EXAMPLE 9

3-methyl-3-glutaric acid

An emulsion of 333.7 g of ditert.-butyl 3-methyl-3-hydroxy-glutarate, 670 ml of demineralized water and 6.7 ml of 22° BACU/e/ hydrochloric acid was stirred at reflux for 5 hours and 166 ml of water were removed by distillation at atmospheric pressure. The mixture was evaporated to dryness under reduced pressure at 40° C. and the product was dried at 40° C. to obtain 144.8 g of product.

A mixture of 144.8 g of the said product and 600 ml of ethyl acetate was heated to reflux and 14 g of activated carbon were added thereto. The mixture was refluxed for 10 minutes and filtered hot and 200 ml of boiling ethyl acetate were added to the filtrate. The mixture was cooled to −10° C. with stirring and held at −10° C. for 30 minutes and was vacuum filtered. The product was washed with 100 ml of ethyl acetate at −10° C. and dried at 40° C. to obtain 112 g of 3-methyl-3-hydroxy-glutaric acid melting at 108° C.

A second crop was obtained by concentrating the mother liquor to about 100 ml, stirring the mixture at −10° C. for 30 minutes and vacuum filtering the mixture. The product was washed with ethyl acetate at −10° C. and dried at 40° C. to obtain 9.72 g of the acid. The latter were dissolved in 48 ml of refluxing ethyl acetate and the solution was cooled to −10° C. and stirred at −10° C. for 30 minutes and vacuum filtered. The product was washed with 10 ml of ethyl acetate at −10° C. and dried at 40° C. for 7.68 g of 3-methyl-3-hydroxy-glutaric acid melting at 108° C.

EXAMPLE 10

3-methyl-3-hydroxy-glutaric acid 146 g of flakes of sodium hydroxide were added all at once at 20° C. to a mixture of 333.7 g of ditert.-butyl 3-methyl-3-hydroxy-glutarate and 2000 ml of water and the mixture was refluxed with stirring for 5 hours to form an emulsion. 200 ml of solvent were distilled off under reduced pressure and the mixture was cooled at 50° C. at which 1400 ml of water were distilled under reduced pressure. The mixture was cooled to 20° C. and the pH was adjusted to 0.5 by addition of 292 ml of 22° BACU/e/ hydrochloric acid. The mixture was evaporated to dryness under reduced pressure to obtain 327.2 g of product containing sodium chloride. A mixture of 327.2 g of the said product and 800 ml of ethyl acetate was refluxed for 15 minutes and after the addition of 12 g of activated carbon, the mixture was filtered hot. The product was empasted twice with 200 ml of boiling ethyl acetate and the filtrate was evaporated under reduced pressure to a volume of 600 ml while heating in a bath of 40° C. The mixture was stirred at −10° C. for 30 minutes and was vacuum filtered. The product was washed with 200 ml of ethyl acetate at −10° C. and dried at 40° C. in an oven to obtain 140 g of 3-methyl-3-hydroxy-glutaric acid melting at 109° C.

A second crop was obtained by concentrating the mother liquor to about 60 ml and the mixture was stirred at −10° C. for 30 minutes and was vacuum filtered. The product was washed with 10 ml of ethyl acetate at −10° C. and dried in an oven at 40° C. to obtain 12.8 g of product which were dissolved in 64 ml of ethyl acetate. The mixture was stirred at −10° C. for 30 minutes and was vacuum filtered and the product was washed with 12.8 ml of ethyl acetate at −10° C. and dried in an oven at 40° C. to obtain an additional 10 g of the said acid.

Various modifications of the process of the invention may be made without departing from the spirit or scope thereof and it is to be understood that the invention is intended to be limited only as defined in the appended claims.

What we claim is:

1. A process for the preparation of 3-methyl-3-hydroxy-glutaric acid of the formula

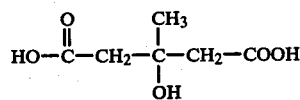

comprising reacting a compound of the formula

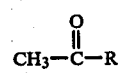

wherein R is selected from the group consisting of alkoxy of 1 to 6 carbon atoms, formyloxy, halogen and acyloxy of 2 to 18 carbon atoms with at least two equivalents of a compound of the formula

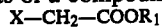

wherein X is an alkali metal and $R_1$ is alkyl of 1 to 6 carbon atoms to obtain a compound of the formula $$\text{R}_1\text{O}-\overset{\overset{\text{O}}{\|}}{\text{C}}-\text{CH}_2-\overset{\overset{\text{CH}_3}{|}}{\underset{\underset{\text{OH}}{|}}{\text{C}}}-\text{CH}_2-\overset{\overset{\text{O}}{\|}}{\text{C}}\text{OR}_1 \qquad \text{IV}$$

and subjecting the latter to saponification or optionally catalytic thermal decomposition to obtain 3-methyl-3-hydroxy-glutaric acid.

2. The process of claim 1 comprising reacting a compound of the formula $$\text{CH}_3-\overset{\overset{\text{O}}{\|}}{\text{C}}-\text{Ra} \qquad \text{IIa}$$

wherein Ra is selected from the group consisting of alkoxy of 1 to 4 carbon atoms, halogen and alkanoyloxy of 2 to 4 carbon atoms with at least two molar equivalents of a compound of the formula
$$\text{X}'-\text{CH}_2-\text{COOR}_{1a} \qquad \text{IIIa}$$
wherein X' is lithium and $R_{1a}$ is alkyl of 1 to 4 carbon atoms to obtain a compound of the formula $$\text{R}_{1a}-\overset{\overset{\text{O}}{\|}}{\text{OC}}-\text{CH}_2-\overset{\overset{\text{CH}_3}{|}}{\underset{\underset{\text{OH}}{|}}{\text{C}}}-\text{CH}_2-\text{COOR}_{1a} \qquad \text{IVa}$$

and subjecting the latter to saponification or thermal decomposition with acid catalyst to form 3-methyl-3-hydroxy-glutaric acid.

3. The process of claim 2 wherein Ra is selected from the group consisting of methoxy, ethoxy, chlorine and acetyloxy, X' is lithium and $R_{1a}$ is selected from the group consisting of methyl, ethyl, and tert.-butyl and the saponification is effected with aqueous sodium hydroxide.

4. The process of claim 3 wherein Ra is chlorine or acetoxy and $R_{1a}$ is tert.-butyl.

5. The process of claim 2 wherein the reaction of compounds of formulae IIa and IIIa is effected at 0° to −80° C. in at least one solvent selected from the group consisting of tetrahydrofuran, dimethylformamide, hexamethylphosphotriamide and methylcyclohexane.

6. The process of claim 1 wherein the compound of formula III is prepared by reacting an alkyl acetate with strong base in a solvent to obtain a solution of the compound of formula III which is reacted directly with the compound of formula II.

7. The process of claim 1 wherein the compound of formula II is added to a solution of the compound of formula III in at least one solvent selected from the group consisting of tetrahydrofuran, dimethylformamide, hexamethyl phosphotriamide and methylcyclohexane.

8. Di-tert.-butyl ester of 3-methyl-3-hydroxy-glutaric acid.

* * * * *